United States Patent [19]

Goble et al.

[11] Patent Number: 5,037,426

[45] Date of Patent: Aug. 6, 1991

[54] PROCEDURE FOR VERIFYING ISOMETRIC LIGAMENT POSITIONING

[76] Inventors: E. Marlowe Goble, 850 E. 1200 North; W. Karl Somers, 651 N. 150 West, both of Logan, Utah 84321

[21] Appl. No.: 246,324

[22] Filed: Sep. 19, 1988

[51] Int. Cl.[5] ............................................. A61B 17/56
[52] U.S. Cl. ........................................ 606/96; 623/13
[58] Field of Search ................ 128/303 R, 92 V, 330, 128/92 R, 92 VD, 92 YF, 92 VK, 898; 623/13, 16, 20; 606/1, 53, 66, 86, 87, 88, 96

[56] References Cited

U.S. PATENT DOCUMENTS

| | | | |
|---|---|---|---|
| 4,632,100 | 12/1986 | Somers et al. | 128/92 YF |
| 4,712,542 | 12/1987 | Daniel et al. | 128/92 VK |
| 4,738,255 | 4/1988 | Goble et al. | 188/92 YF |
| 4,772,286 | 9/1988 | Goble et al. | 623/16 |

Primary Examiner—C. Fred Rosenbaum
Assistant Examiner—William W. Lewis
Attorney, Agent, or Firm—M. Reid Russell

[57] ABSTRACT

For knee reconstruction surgery involving replacement of an anterior or posterior cruciate ligament the present invention is in a process for verifying isometric ligament positioning at the femoral and tibial points of origin that includes, as apparatus, an arrangement of a stud (19) with attached suture (24) to serve as a mock ligament for testing isometry. In practice, as for an anterior cruciate ligament replacement procedure, a surgeon, observing on a fluoroscopic monitor (17), forms a tibial tunnel (18) from a point medial to the tibial tuberosity that exits a test or proposed tibial point of ligament origin. The stud (19) is arranged for turning on a driver (20) that is then passed through that formed tunnel and the stud is turned into the test or proposed femoral point of ligament origin. The driver (20) is then pulled out of engagement with the stud (19) exposing the suture (24) that extends from that stud, which suture (24) is attached under tension to a tension isometer (25) and the knee (10) is flexed through its full range of motion. With an isometrically correct selection of the femoral and tibial ligament points of origin, the tension isometer (25) will show no more than a three (3) pound change in force and no more than a two (2) mm change in ligament length or distance between the two points of origin over a full range of knee (10) flexure.

2 Claims, 5 Drawing Sheets

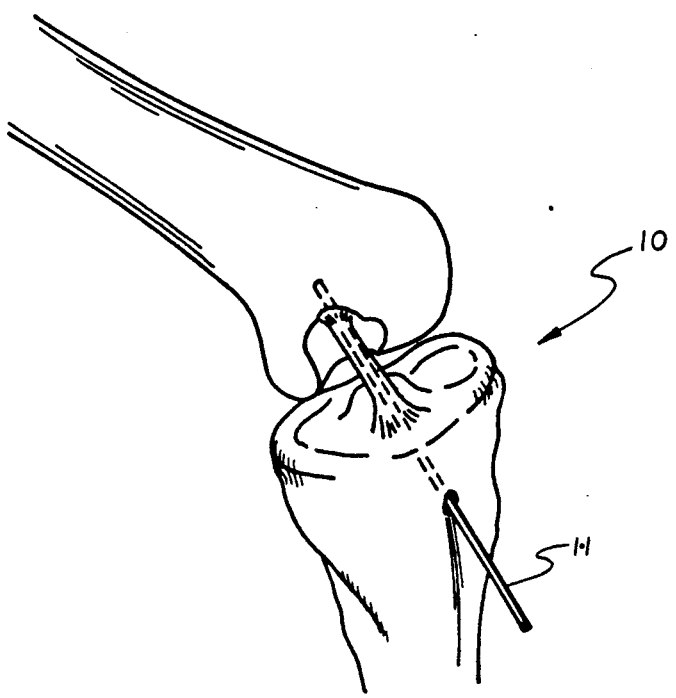
Fig. 1
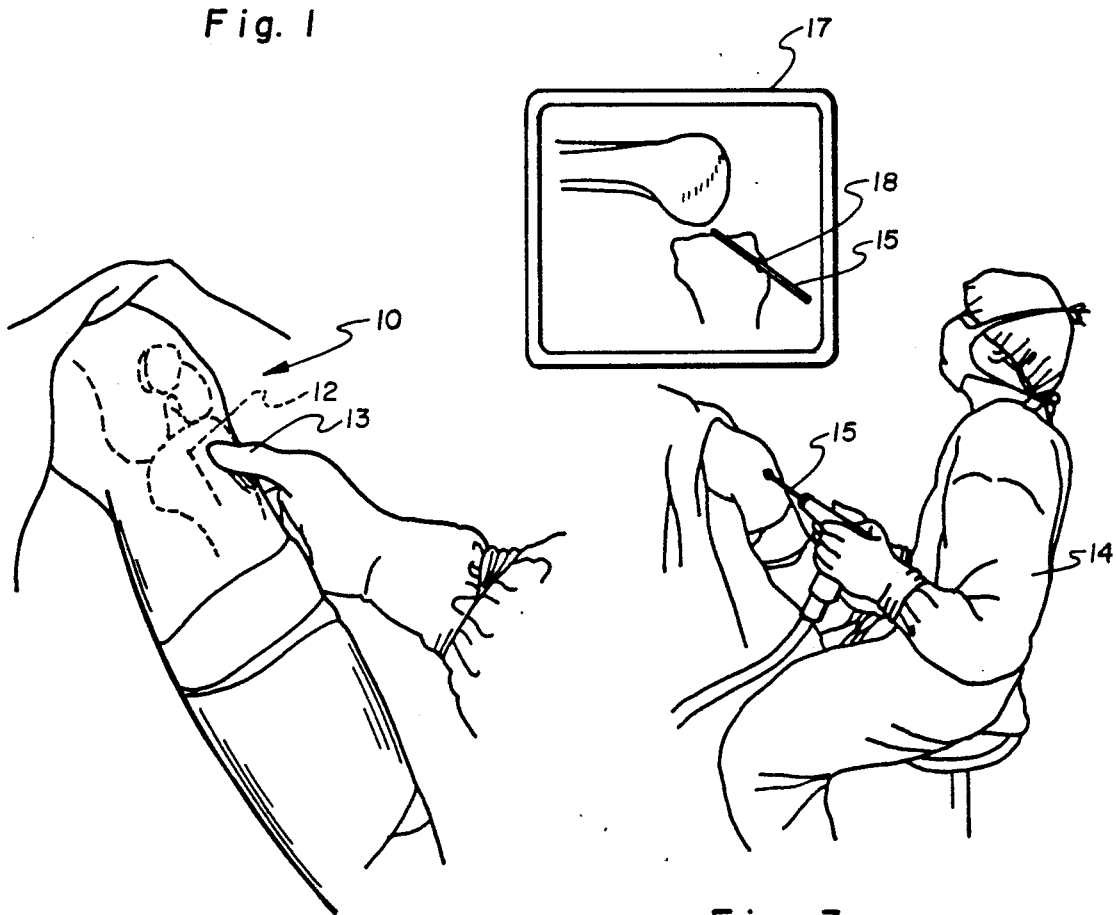
Fig. 2
Fig. 3

PROCEDURE FOR VERIFYING ISOMETRIC LIGAMENT POSITIONING

BACKGROUND OF THE INVENTION

1. Field of the Invention

The present invention relates to arthroscopic surgical procedures for ligament reconstuction and particularly to apparatus and a procedure for isometrically locating either an anterior or posterior cruciate ligament femoral and tibial points of attachment.

2. Prior Art

In anterior and posterior ligament replacement surgery both ligament tension and positioning of that ligament between tibial and femoral surfaces must be optimumized for a successful surgery. Prior to the present invention such positioning involved a surgeon utilizing a flurorescopic monitor or visually forming a tunnel to pass through the approximate ruptured ligament tibial and femoral points of origin, and attaching a ligament therein to test for correct isometry. An example of such procedure is shown in a patent to Daniel, et al., U.S. Pat. No. 4,712,542. If the ligament positioning was found not to be isometrically correct the tunnel had to be altered or reformed until correct isometry was obtained. Essentially, a trial and error procedure with the surgeon's skill determining the outcome.

Unlike the trial and error process set out above, the present invention provides a process for testing femoral and tibial ligament origin points that is both accurate and minimally invasive. The procedure further utilizes a mock ligament and a tension isometer to measure, when the knee is flexed through a full range of motion, a change in tension of no more than a certain force verifying proper isometric selection of the femoral and tibial points of origin.

SUMMARY OF THE INVENTION

It is a principal object of the present invention to provide apparatus and a surgical procedure for knee ligament replacement surgery for determining optimum femoral and tibial anterior and/or posterior cruciate ligament points of origin whereafter a surgeon can form finished femoral and tibial tunnels through those points and maintain a ligament under tension therein.

Another object of the present invention is to provide, as apparatus for performing the surgical procedure, an isometric testing stud, with attached suture for use as a mock ligament, for turning into a bone surface at a test posterior or anterior point of origin, the suture to extend therefrom through a tunnel in the opposite bone that has, as its one end, the other test point of origin, the suture free end to fit through the tunnel for connection to a tension isometer for measuring applied tension at different knee positions.

Still another object of the present invention is to provide apparatus and process for locating the isometric tibial and femoral points of origin on the opposing bone surface for an anterior or posterior cruciate ligament that is performed fluoroarthroscopically and is minimally invasive.

The present invention is an apparatus and procedure for locating and testing for proper isometry test points of origin for a cruciate ligament. With the test points located, a tunnel that consists of aligned or divergent tunnel segments formed through the respective distal femoral and proximal tibial bone ends, intersecting the points of origin. In practice, once the proper tunnels through points of origin are properly formed to receive the ligament, with one end of the ligament secured in place, a desired tension is applied to the other ligament end, and that end is then secured in place. Assuming that the ligament is properly aligned through the correct ligament points of origin, this tensioning is routine.

It is, therefore, the locating of the ligament points of origin on the femoral and tibial surfaces that is critical to the success of the procedure. Through experimentation, for replacement of the anterior cruciate ligament, it has been determined that the femoral origin will be approximately three (3) mm anterior to the junction of the posterior cortex and the intercondylar seam; with the site of the tibial origin at a point that is approximately one third of (⅓) the anteroposterior distance posterior to the anterior tibia, or approximately eighteen (18) to twenty two (22) mm posterior to the front of the bony tibia. In the replacement of a posterior cruciate ligament the tibial point of origin has been determined to be at the posterior margin of the mid-portion of the tibial plateau and the femoral point of origin is located within the intercondylar notch at varying points in the medial femoral condyle. These are the approximate points that a tunnel needs to pass through to provide for proper replacement of an anterior or posterior cruciate ligament with either a biologic graft or prosthetic ligament.

For performing this procedure the present invention preferably employs an isometric testing stud with attached suture that may be like the self-drilling and tapping titanium metal stud shown in a U.S. Pat. No. 4,632,100 that the present inventors are the inventors of. Though, it should be understood, other arrangements of isometric testing studs with radio-opaque fabric, or metal sutures, or the like, can be used for the described procedure.

For replacement of an anterior cruciate ligament the isometric testing stud is inserted through a medial parapatellar arthroscopy tunnel or portal that is passed through the test or intended tibial point of origin. Which isometric testing stud is turned by a driver into the test femoral point of ligament origin. The driver is then removed by pulling it back through the tunnel. In that driver removal, which is contained in the driver and attached on one end of the stud, is thereby pulled from the driver as the driver is removed from the tunnel or portal. The suture free end is then attached under tension to a tension isometer. To test for proper isometry, the patient's knee is flexed appropriately through its full range of motion, with differences in tension shown on the tension isometer. If there is less than a three (3) pound change in tension over the full range of knee motion the selected test femoral and tibial point of origin are confirmed as being correct.

When correct femoral and tibial point of origin selection is verified the isometric testing stud is turned out of the bone and the knee is drilled with successively larger drills until a tunnel of sufficient diameter to accommodate a replacement ligament is available. One ligament end is secured within a cortex tunnel end and the other end of the ligament is secured to the bone surface. A U.S. Pat. No. 4,772,286 that the present inventors are the inventors of show a process for attaching an anterior cruciate ligament within such tandem tunnels in knee reconstruction surgery.

BRIEF DESCRIPTION OF THE DRAWINGS

These and other objects and features of the present invention will become more fully apparent from the following description in which the invention is described in detail in conjunction with the accompanying drawings.

FIG. 1 is a side elevation view of the distal femur and proximal tibia bone ends showing a longitudinal section of the distal femur removed to the intercondylar notch, and showing a "K" wire inserted from the anterior medial tibia through the anterior cruciate ligament, to illustrate the femoral and tibia points of ligament origin;

FIG. 2 is a side elevation view of a patient's leg, the knee shown flexed at approximately a ninety (90) degree angle with a vertical line above the tibial tuberosity shown in broken lines;

FIG. 3 is a side elevation view of a surgeon observing a monitor and positioned in front of the knee of FIG. 2, drilling a tunnel from the tibial tuberosity that is shown on the monitor exiting the ligament tibial origin;

DETAILED DESCRIPTION

Figure 4:
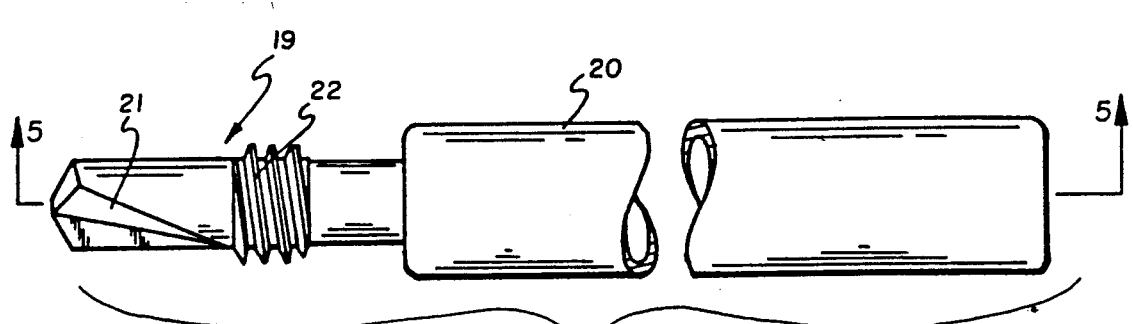
FIG. 4 shows a side elevation view of a suture anchor for use as an isometric testing stud with driver therefore.

In knee reconstruction surgery it is recognized that the surgical procedure should be minimally invasive and yet be adequate to accomplish the goal to accurately re-establish the patient's four bar chain-like system. To this end the surgical entrance should be of minimal size to avoid unnecessary pain, poor cosmoses, and loss of normal joint proprioception. Further, the procedure should be performed in minimal time to limit tourniquet application time. The present procedure addresses and meets these needs and considerations.

FIG. 1 is included to illustrate that an optimum ligament replacement of an anterior cruciate ligament in knee 10 involves exactly connecting the replacement ligament, either a biologic graft or prosthetic, at the femoral and tibial points of origin. This is illustrated by the arrangement of a pin or drill 11 that is shown passed through the ligament and its points of origin. Unfortunately, a ligament rupture necessitating the procedure may involve a separation of the ligament end from the bone surface making it difficult or impossible to determine a point of origin, particularly when that point of origin must be determined viewing a fluoroscopic monitor.

Human cadaveric dissections have revealed the precise points of attachment as are necessary to achieve a "check rein" replacement for a deficient anterior cruciate ligament. Experimentally, as viewed from a lateral knee radiograph, the isometric anterior cruciate ligament femoral origin is at a point that is approximately three (3) mm anterior to the junction of the posterior cortex and the intercondylar seam, with the site of the isometric tibial insertion located at a point that is approximately one third ($\frac{1}{3}$) of the anteroposterior distance posterior to the anterior tibia, or approximately eighteen (18) to twenty two (22) mm posterior to the front of the bony tibia. These insertion points are, as shown in FIG. 1, for the anterior cruciate ligament. For the posterior cruciate ligament the points of origin are similarly determined and, it should be understood, the present process is applicable to both cruciate ligament replacement. Of course, the points of origin and tunnels are appropriately selected and formed for the particular cruciate ligament being replaced.

In FIG. 2 the knee 10 is shown in broken lines. Therein, a vertical broken line 12 located alongside a surgeon's thumb 13 marks a point above the tibial tuberosity that is the target for forming the tibial tunnel, as shown in FIG. 3. In FIG. 3 a surgeon 14, seated in front of knee 10 that is flexed to approximately one hundred ten (110) degrees, operates a drill 15 as he observes on a fluoroscopic monitor 17 drill end 16 progress into knee 10. Shown on the fluoroscopic monitor 17, the drill end 16 has passed into a medial point on the anterior tibial tuberosity and exits the test tibial point of origin of the anterior cruciate ligament forming tibial tunnel 18. Which tunnel exiting the test tibial point of origin is directly opposite to the test femoral point of origin of the ligament. The tunnel 18 is of a diameter to just accommodate a self-tapping suture anchor stud 19, that is also known as an isometric testing stud; hereinafter referred to as stud, and driver 20, shown in FIGS. 4 and 5.

To locate the test or trial tibial and femoral points of origin, with the tibial tunnel 18 formed as set out above, the stud 19 is mounted on the end of driver 20 and passed into the tunnel. The surgeon guides the stud and driver by observing the fluoroscopic monitor 17 to where a stud drill 21 pointed end engages the femur at what the surgeon believes to be the femoral isometric point of origin. The stud 19 is then carefully turned into the bone, until medial self-tapping screws 22 that follow the drill end are fully turned into the bone, the stud rearmost end 23 coming to rest proximate to or aligned with the bone surface. Thereafter, the driver 20 is pulled out from engagement within the stud 19, leaving a double strand radio-opaque flexible suture 24, hereinafter referred to as suture, extending therefrom. Which suture is connected on its end and extending from the stud rearmost end 23. The suture 24 is thereby pulled from the driver to without the tibial tunnel 19. The suture 24 is to function as a mock anterior cruciate ligament for verifying that the selected tibial and femoral points of origin are isometrically correct.

Figure 6A:
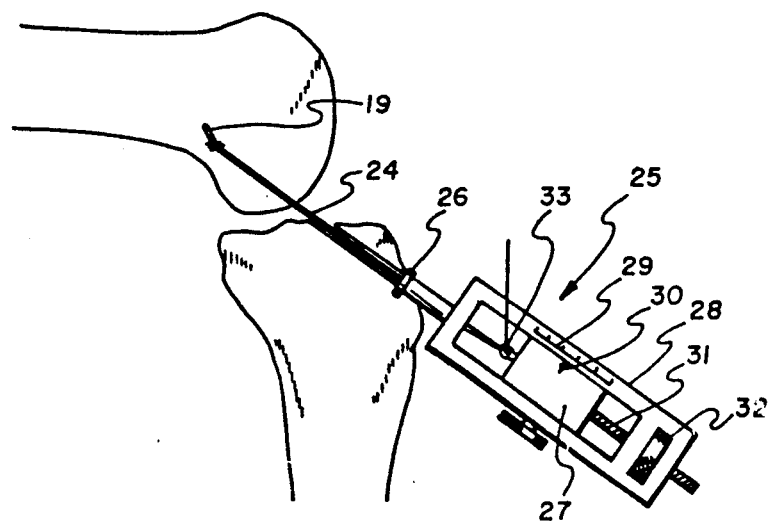
FIG. 6A shows the knee of FIGS. 2 and 3 with the suture anchor of FIG. 4 fitted through the tibial tunnel of FIG. 3 and turned into the femur at the ligament femoral origin, the suture thereof shown connected to a tension isometer.
Figure 6B:
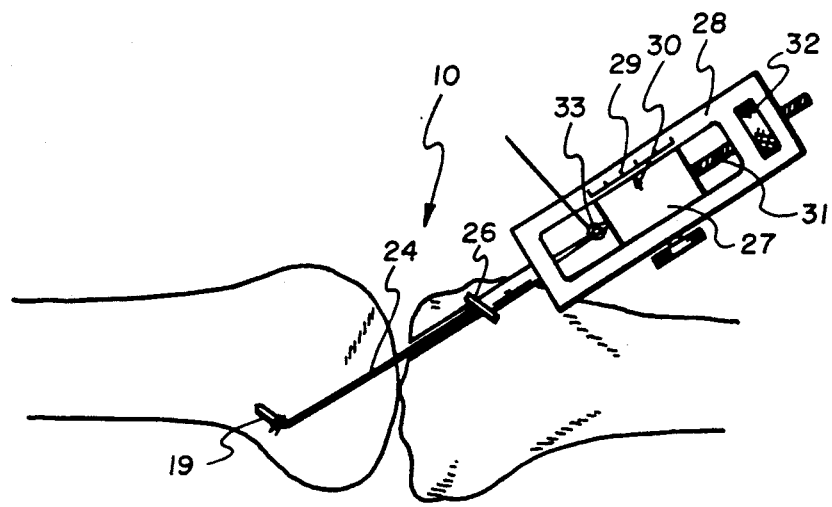
FIG. 6B shows the knee of FIG. 6A in a straightened attitude.

To determine that the tibia tunnel 18 end and selected femoral point are the true isometric points, the mock ligament or suture 24 end is connected, under appropriate tension, to a tension isometer, as shown in FIGS. 6A and 6B. With a certain preload on the scale of the tension isometer the knee is flexed through appropriate angular configurations and the exerted forces at the various knee attitudes are measured. For correct isometry there will be no more than a three (3) pound change in force and no more than a two (2) mm change in suture length or distance between the tibial and femoral points of origin, through a full range of knee motion. For example, FIGS. 6A and 6B show a tension isometer 25 as including a tilting collar 26 that is for butting against the tibial tunnel entrance and wherethrough suture 24 is fitted and attached to a block 27. Block 27 is preferably arranged to travel within a housing 28 of the isometer. Housing 28 is open at one face to expose the block with sequential numbering 29 scribed along the housing face adjacent to the one edge of block 27, with a pointer 30 scribed on the adjacent block 27 edge, at its approximate mid-point. The pointer 30 is to point to a number 29 to indicate a force that is being applied on the block that is in opposition to a spring biasing acting on the block, not shown. The block 27 position or force applied thereto can further be preset to a certain force by operation of a set screw arrangement consisting of a threaded rod 31 that is turned through a caged manually turnable collar 32. The end of threaded rod 31 to butt against a block 27 and the suture is shown tied through a ring 33 on the opposite block end to pull that block against its spring biasing, as reflected by the positioning of pointer 30 relative to the scale 29. So arranged, as the tension on suture 24 is increased and decreased during knee movement through its full range of motion, that change is reflected as a greater or lesser force relative to the pre-set value or force on the tension isometer.

In practice, as illustrated in FIG. 6A, with the knee maintained at approximately a ninety (90) degree angle, the suture is attached under tension to the tension isometer 25, as set out above. The knee is then flexed through its full range of motion, to include a full extension as shown in FIG. 6B. During that knee flexure forces exerted on suture 24 are displayed on the tension isometer 25 as a change in position of pointer 30 relative to scale 29. For a correct selection of femoral and tibial points of origin, there will be no more than a three (3) pound change in force and no more than a two (2) mm change in ligament length or the distance between the points of origin throughout a full range of knee motion. A missed selection of one or both points of origin will show up as a much larger force differential. For example, in a cadaver study, where the femoral origin was placed just three (3) mm anterior to the desired isometric point, in full extension a large force and progressive elongation of the mock ligament occurred to a flexion of approximately ninety (90) degrees whereat an added or differential force of twenty five (25) pounds of tension was recorded and the mock ligament failed.

Also, of course, where the ligament undergoes laxity, such is also unacceptable. Accordingly, a femoral origin placement where the placement is passed or "over the top" of the isometric point was found to result in progressive anterior laxity in flexion. Experimentally, with a pre-load of ten (10) pounds at ninety (90) degrees flexion, there was no force shown on the tension isometer, with laxity further progressing as the knee was flexed to one hundred forty (140) degrees.

Figure 7:
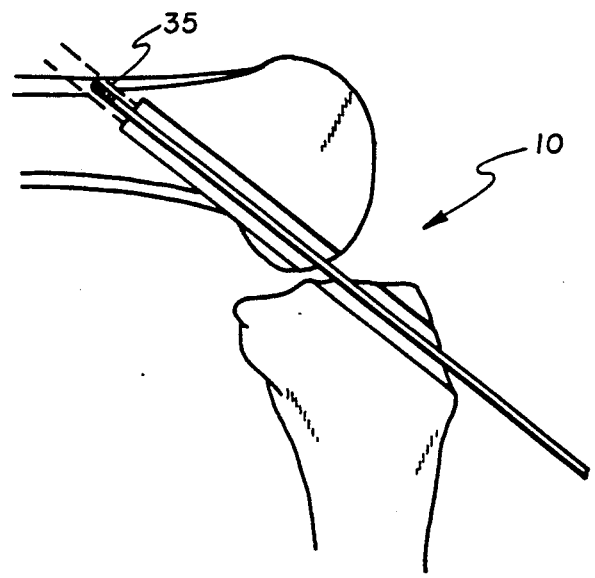
FIG. 7 shows the knee of FIGS. 2 and 3 after aligned tunnels have been drilled through the femoral and tibial ligament origins and femur cortex to receive a ligament installed therein.

As set out above, locating test or trial points of origin and attaching the stud 19 with sutures 24 extending therebetween, as a mock ligament, enables a reliable and precise test of isometry before the ligament tunnel is formed. Accordingly, it is desirable that the initial tibial tunnel and femoral site wherein the stud 19 is turned be as narrow as possible. So arranged, where an erroneous point of origin is selected, the test will be minimally invasive facilitating a reselection of another femoral point or even a redrilling of the tibial tunnel 18 without an appreciable weakening of the bone integrity. With the femoral and tibial isometric points determined the tibial tunnel 18 can be enlarged and a tandem femoral tunnel formed, as shown in FIG. 7. The femoral cortex at 35 is then tapped, the tandem tunnels to receive the ligament.

Figure 5:
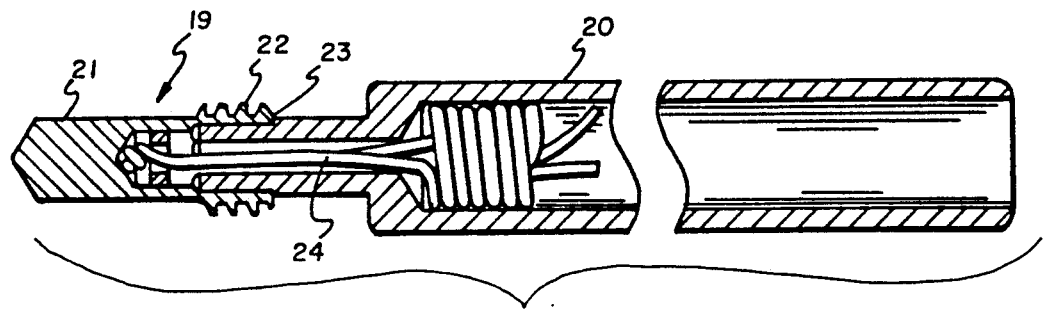
FIG. 5 shows a sectional view taken along the line 5—5 of FIG. 4.
Figure 8:
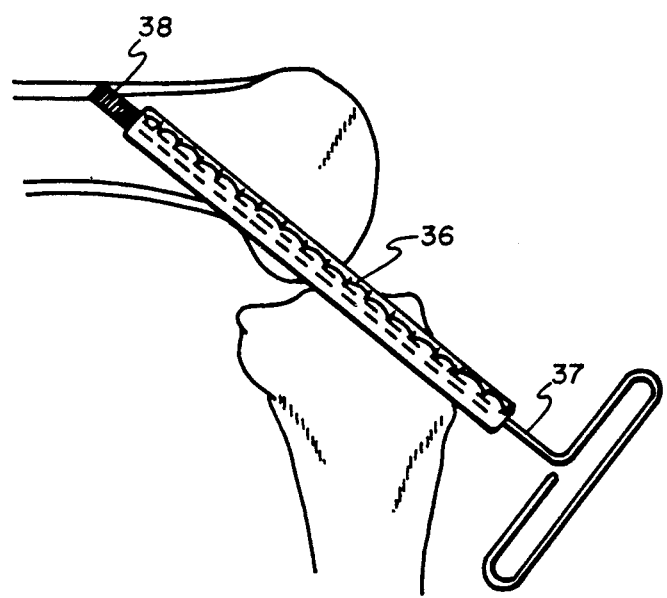
FIG. 8 shows an allograft ligament mounted to a driver being installed in the tandem tunnels of FIG. 7, with a threaded connector shown attached to the ligament end for turning in a tapped hole formed in the femur cortex.

FIG. 8 shows an allograft ligament 36 that has been rolled around a driver 37 and sutured and includes a threaded fitting 38 secured to the ligament end that has been turned in the tapped cortex 35, securing the one allograft ligament 36 end thereto. The other allograft ligament 36 end is secured to the tibia cortex as with a staple or staples, not shown, after the handle 37 has been pulled out from the ligament roll and a desired tension force applied to that ligament. Of course, other arrangements of biologic grafts or prosthetic ligaments can be utilized as can other arrangements for securing them under tension, within the scope of this disclosure. Further, it should be understood, the described procedure and components are applicable to a surgical replacement of the posterior cruciate ligament allowing, of course, for different tunnel forming as are appropriate for a posterior cruciate ligament replacement.

Where the stud 19 has been found in practice to be usable as a mock ligament, it is recognized that another configuration of a isometric testing stud and driver than those shown in FIGS. 4 and 5 could also be used. Accordingly, the present invention is also directed to another embodiment of an isometric testing stud 40 shown in FIGS. 9 and 9A and to a still another embodiment of an isometric testing stud 50, shown in FIGS. 10 and 10A.

Figure 9:
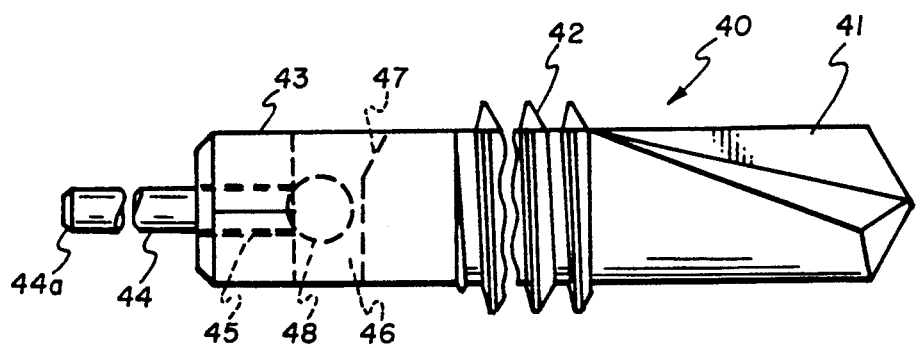
FIG. 9 is a side elevation view of another embodiment of an isometric testing stud that includes a suture wire for use as a mock ligament in practicing the process of the present invention.
Figure 9A:
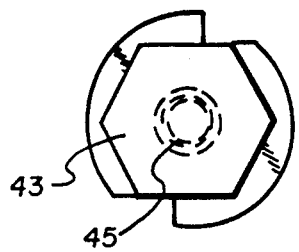
FIG. 9A is a rear end view of the isometric testing stud of FIG. 9.

FIG. 9 shows the isometric testing stud 40, hereinafter referred to as stud, that is substantially like the stud 19 of FIGS. 4 and 5. Like stud 19, stud 40 includes a fluted drill end 41 and medial cutting threads 42. Distinct from the stud 19, stud 40 includes a hex-shaped rear end 43 that is to receive a driver, not shown, fitted thereover, the stud 40 and driver to otherwise function as does the driver 20 with stud 19 of FIGS. 4 and 5. Further distinct from stud 19, stud 40, at its hex end, to accommodate a wire suture 44, is drilled longitudinally at 45, as shown in FIG. 9A, and includes a lateral hole 46 that is shown in broken lines in FIG. 9, intersecting that longitudinal hole 45. The lateral hole 46 is shown at 47 sloped towards the fluted drill end 41, which slope is to guide the suture wire end 44a into and through longitudinal hole 45. The wire suture 44 is further shown in broken lines to include a bead 48 that is formed on its other end that is of greater diameter than the longitudinal hole 45. So arranged, the wire suture 44 is fitted through the longitudinal hole 45 to the bead 48 end that butts against the edge of longitudinal hole 45, blocking travel therethrough. The wire suture 44 is thereby fixed to the stud 40 and is, in turn, fitted longitudinally through the driver, not shown, to function like the suture 24 described as a mock ligament.

Figure 10:
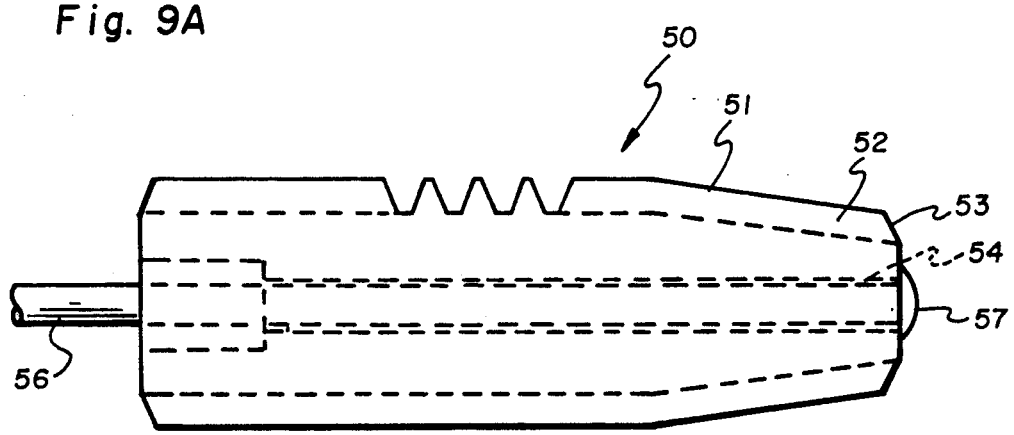
FIG. 10 is a side elevation view of still another embodiment of an isometric testing stud for use as a mock ligament in practicing the process of the present invention.
Figure 10A:
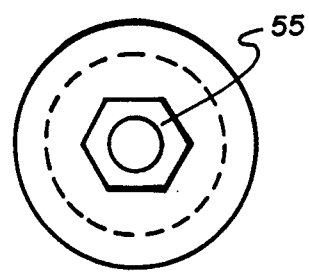
FIG. 10A is a rear end view of the isometric testing stud of FIG. 10.

FIGS. 10 and 10A show still another embodiment of an isometric testing stud 50, hereinafter referred to as stud. Stud 50, like the above-described studs 19 and 40 is for implanting, by the above-described process, at a designated femoral or tibial point of ligament origin, with a suture extending therefrom that serves as a mock ligament for connection to a tension isometer. Unlike the above-described studs 19 and 40, stud 50 does not include a drill end and in use, a hole must be formed into the bone surface of a diameter and depth to where the stud screw threads 51 will turn in that formed hole. Preferably, stud 50 includes the threads 51 formed therearound over its entire length from a tapered nose end 52. Shown in FIG. 10, the stud nose end 52 tapers outwardly from a first tooth starting edge 53 that, when the stud is turned into a hole formed into a bone surface, will bite into that bone surface, the teeth 51 turning also into that bone.

Figure 11:
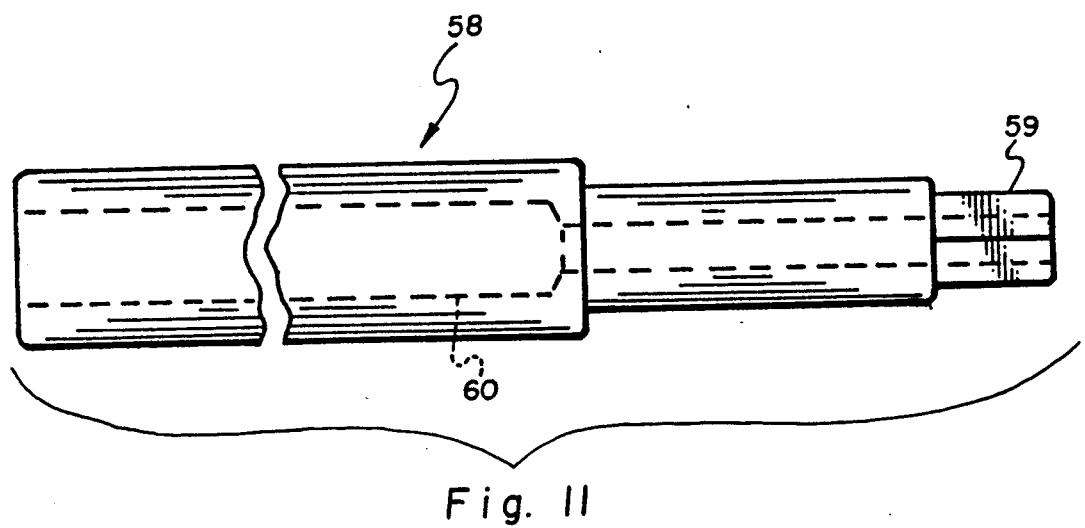
FIG. 11 is a side elevation view of a driver for coupling at a hexagonal shaped end thereof into the isometric testing stud of FIGS. 10 and 10A, and showing, in broken lines, a longitudinal cavity formed therethrough.

Shown in broken lines in FIG. 10, the stud 50 is holed longitudinally from end to end at 54, which hole 54, at a rearmost end, is enlarged to have hexagonal shaped walls 55. The hexagon shaped opening walls 55 are to receive a hexagonal end 59 of a driver 58. Shown in FIG. 11, for guiding the stud on the end thereof through a prepared femoral or tibial tunnel and into the hole formed in the opposing bone surface for turning therein. From the hexagonal walled end 55 the longitudinal hole 54 is to accommodate a suture, either fabric or wire fitted therethrough. As shown in FIG. 10, the suture that is preferably wire 56, is fitted through hole 54 and through a longitudinal center passage 60, shown in broken lines, through driver 50 and includes a button 57 secured across the wire end. The button 57 has a diameter that is greater than the diameter of the longitudinal hole 54, prohibiting the withdrawal of the suture wire 56 therethrough.

As set out above, the tandem tibial and/or femoral tunnels for testing for proper ligament isometry are preferably as narrow a diameter as practical. With the suture attaching arrangements of studs 40 and 50 with their drivers, a small diameter of tool is achieved. Where, as in the case of the stud 50, the driver end is fitted into the stud an even smaller diameter of driver can be utilized. In practice, studs 40 and 50 have been constructed to have, respectively, diameters of from $\frac{3}{8}$ inch for stud 40, and $\frac{1}{4}$ inch for stud 50. Stud 40, of course, requires a driver of greater diameter to fit over the hexagonal end 43 thereof.

While a preferred embodiment of a process and embodiments of apparatus for practicing that process have been shown and described herein, it should be apparent that the present disclosure is made by way of example only and that variations are possible within the scope of this disclosure without departing from the subject matter coming within the scope of the following claims, which claims we regard as our invention.

We claim:

1. A process to verify proper isometric ligament positioning in an arthroscopic surgical procedure on a human knee to replace the anterior or posterior cruciate ligament as performed by a surgeon viewing a fluoroscopic monitor, comprising the steps of, with a patient's knee maintained appropriately forming a test passage from a point on the anterior medial portion of the tibia for an anterior cruciate ligament replacement or of the femur for a posterior cruciate ligament replacement, through the bone to intersect and pass through a first proposed or test ligament point of origin; guiding an isometric testing stud means mounted to the end of a driver through the passage and turning it into the bone at a second proposed or test ligament point of origin on the femur for an anterior cruciate ligament replacement or on the tibia for a posterior cruciate ligament replacement; pulling the driver out of engagement with the isometric testing stud means and withdrawing said driver out of said test passage exposing a suture means connected to the exposed end of said isometric testing stud means; connecting, under tension, said exposed portion of said suture means to a tension isometer that will read a load condition on said suture; flexing the knee through its full range of motion; and observing the tension isometer during that knee flexure, where providing the proposed or test points of origin are isometrically correct, there will be no more than a three (3) pound change in tension on said suture means.

2. A process as recited in claim 1, wherein through a full range of knee flexure there will be no more than a two (2) mm change in the suture means length or distance between the test points of origin for an isometrically correct selection of points of origin.

* * * * *